United States Patent [19]

Brubaker et al.

[11] Patent Number: 5,163,333
[45] Date of Patent: Nov. 17, 1992

[54] BACK AND TRUNK POSITIONING AND SHAPE SENSING APPARATUS

[75] Inventors: Clifford E. Brubaker, Charlottesville; Colin A. McLaurin, Crozet, both of Va.

[73] Assignee: The Center for Innovative Technology by mesne assignment from the University of Virginia, Herndon, Va.

[21] Appl. No.: 618,911

[22] Filed: Nov. 28, 1990

[51] Int. Cl.⁵ .................. G01B 21/20; G01B 21/30; B25J 11/00; B66F 19/00
[52] U.S. Cl. .................. 73/865.8; 414/589; 414/779
[58] Field of Search .......... 73/865.8, 104, 105; 414/589, 590, 779–782, 784

[56] References Cited

U.S. PATENT DOCUMENTS

| | | | |
|---|---|---|---|
| 3,612,456 | 10/1971 | Palmer | 73/105 X |
| 3,805,651 | 4/1974 | Smorenburg | 414/784 X |
| 4,391,360 | 7/1983 | Minnetti | 414/590 X |
| 4,671,721 | 6/1987 | Pratt et al. | 414/590 X |
| 4,781,517 | 11/1988 | Pearce et al. | 414/590 |
| 4,890,235 | 12/1989 | Reger et al. | 364/413.01 X |

FOREIGN PATENT DOCUMENTS

| | | | |
|---|---|---|---|
| 108658 | 8/1979 | Japan | 73/865.8 |
| 3001 | 1/1986 | Japan | 73/865.8 |
| 28801 | 2/1986 | Japan | 73/865.8 |
| 554408 | 4/1977 | U.S.S.R. | 73/865.8 |

Primary Examiner—Tom Noland
Attorney, Agent, or Firm—Staas & Halsey

[57] ABSTRACT

An apparatus for positioning and holding an individual in a prescription posture followed by a determination of the surface contour of the posterior trunk. The positioning utilizes an array of adjustable pads arranged in rows. The shape sensing is accomplished by tracing a transverse cross-section of the posterior half of the trunk, at serial increments along the vertical axis of the trunk. The tracing is based on angular orientation, linear displacement and vertical elevation of a sensor mounted on a radial arm.

18 Claims, 7 Drawing Sheets

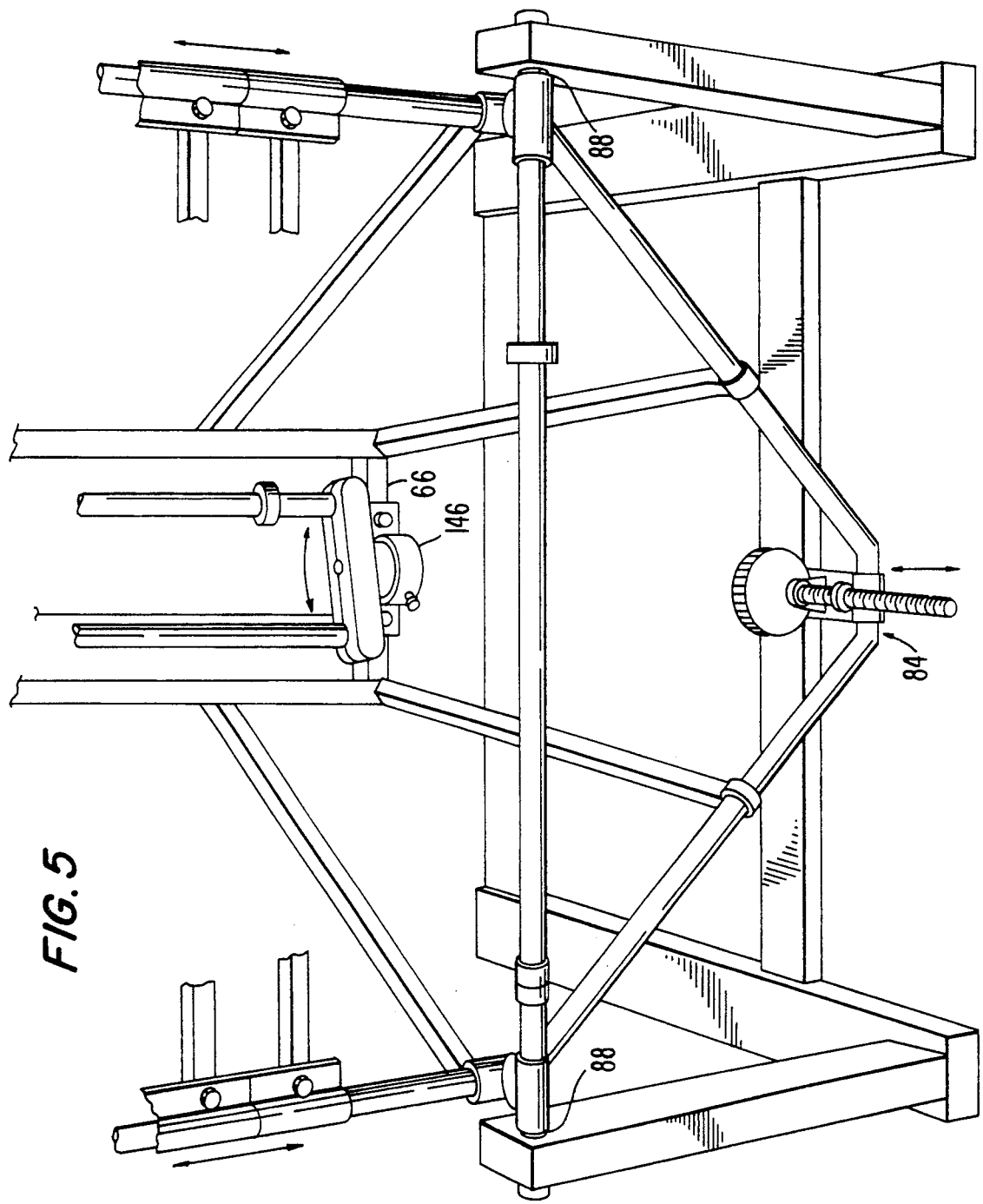

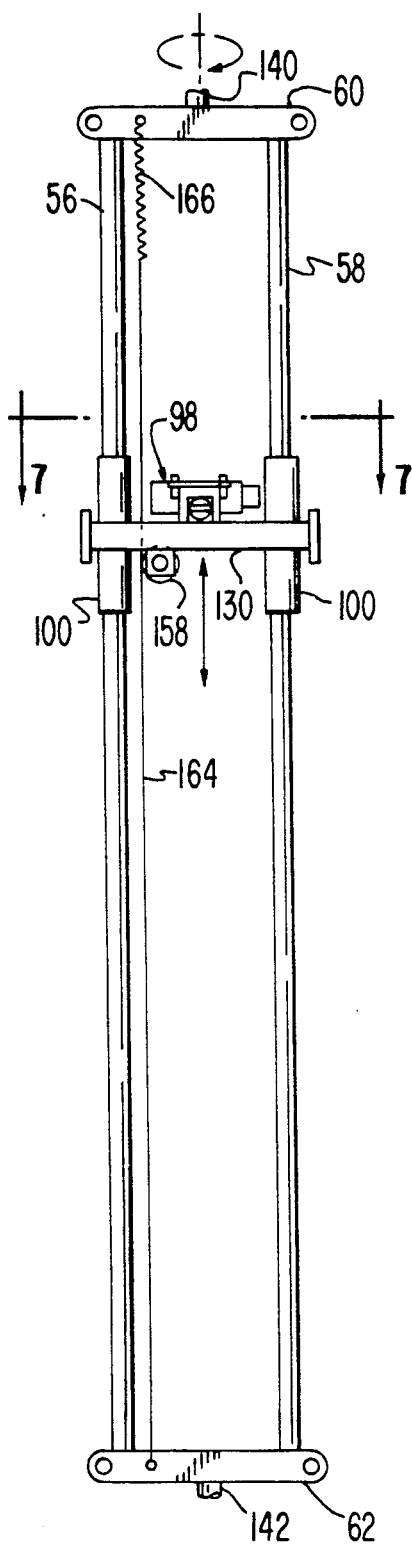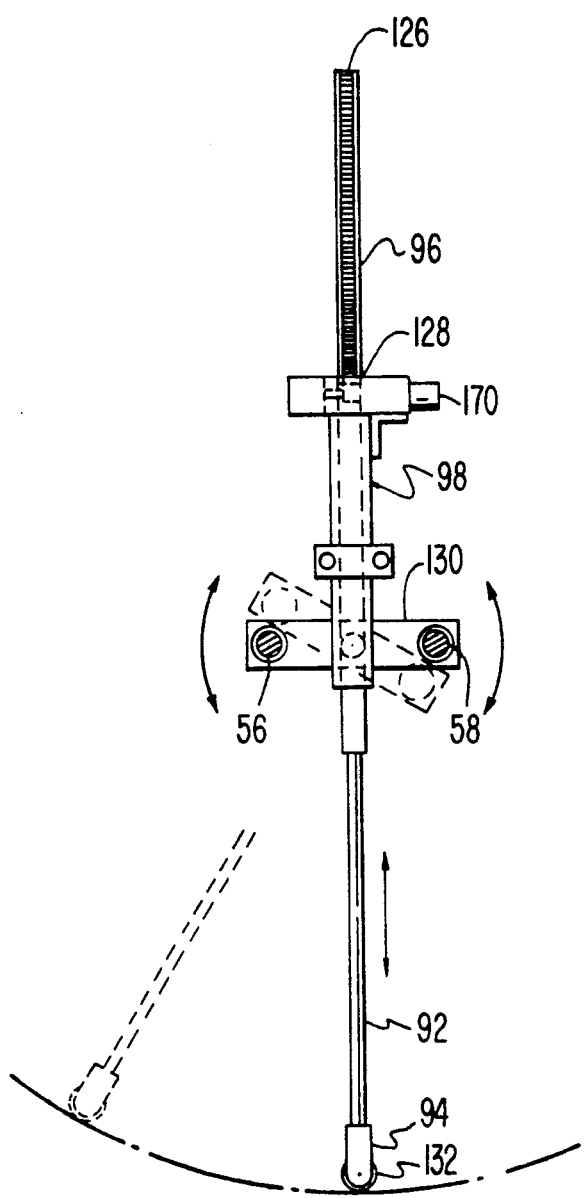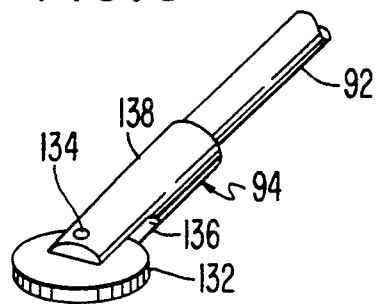

BACK AND TRUNK POSITIONING AND SHAPE SENSING APPARATUS

BACKGROUND OF THE INVENTION

This invention relates to an apparatus for positioning the back and trunk in a sitting position and then measuring the shape of the back and trunk when so positioned.

Body-supporting seats are especially important to persons with neuro-muscular disorders and physical deformities who must be seated for long periods of time. Therefore, customized, comfortable and usable seating is of special value for these persons and such seating must provide suitable positioning and support.

A common present technique for providing a customized shape is based on a dilatency casting technique, where the impression of a person's shape is obtained with a "bean bag" and a vacuum drawn on the bean bag to maintain the "beans" in the position to which they have been impressed. A plaster cast is formed over the contour of the vacuum bag, which is used to form a positive mold. This mold is subsequently used to fabricate a support surface, such as a brace, seat, seat back, etc. This technique obscures the individual and makes it difficult to determine the state of posture or to control the posture while the impression is taken. Other techniques for providing a customized back and trunk seating arrangement have also been used.

The present invention includes an array of positioning fixtures that provide complete flexibility in positioning an individual and maintaining a desired posture. The invention then enables the determination of complex three-dimensional contours of the individual's body surface, and provides an accurate, inexpensive and quick assessment and determination of the contours to enable the subsequent fabrication of the customized body support. The invention has an additional application as a diagnostic instrument to determine anomalous contours and spinal deformities.

The shape sensed by the invention can be stored to determine changes resulting from growth, progression of a pathology, pre- and post-interventions, etc. The invention provides the capability of positioning and holding an individual in a prescription posture where the surface contour of the posterior trunk may be determined.

The positioning is accomplished with an array of adjustable pads arranged in rows, and the apparatus has a total of five degrees of freedom. These include: tilt adjustment of the frame to establish the back plane; vertical adjustment of the positioning pad by rows; individual lateral and depth adjustments of individual pads; and rotation of the pads individually about a vertical axis.

The shape sensing is accomplished by tracing a transverse cross-section of the posture half of the trunk at serial increments along the vertical axis of the trunk. The tracing is based on the angular orientation, linear displacement, and vertical elevation of a radial arm. The frequency of data points is arbitrary. More or fewer points can be measured according to the severity of the curvature within a particular region.

Once the shape has been determined, this information can be used to produce a customized back and trunk support for the individual. One way of doing this which may be used with the present invention would be by digitizing the shape sensed by the electromechanical transducer of the present invention using an analog-to-digital converter, and enter the information into a digital computer. The computer can be used to control a continuous numerical control (CNC) three-axis milling machine for carving the contour of the back and trunk directly into a material of choice, similar to that shown in the co-pending application of Brubaker et al. for making seat cushions (entitled CUSTOM CONTOURED WHEELCHAIR SEAT AND OTHER BODY SUPPORTS, filed Mar. 9, 1989, U.S. Ser. No. 07/320,959) and now abandoned which was split into U.S. Ser. No. 07/652,442 filed Feb. 6, 1991 as a file rapper continuation application and U.S. Ser. No. 07/633,056 filed Dec. 24, 1990 as a divisional application and now abandoned. Pending U.S. Ser. No. 07/652,442 is incorporated herein by reference.

For a better understanding of the nature of the present invention, reference should be had to the accompanying drawings and the detailed description below.

BRIEF DESCRIPTION OF THE DRAWINGS

FIG. 5 is a perspective view of the bottom of FIG. 1 from the front, showing the tilt adjustment arrangement and other adjustable features;

FIG. 6 is a front view of the vertical parallel adjustment rods for determining the vertical positioning of the shape sensor;

FIG. 7 is a top view of the shape sensor taken on Section 7—7 of FIG. 6;

FIG. 8 is a broken-away detailed perspective view of the end of the shape sensor;

DESCRIPTION OF THE PREFERRED EMBODIMENT

Figure 1:
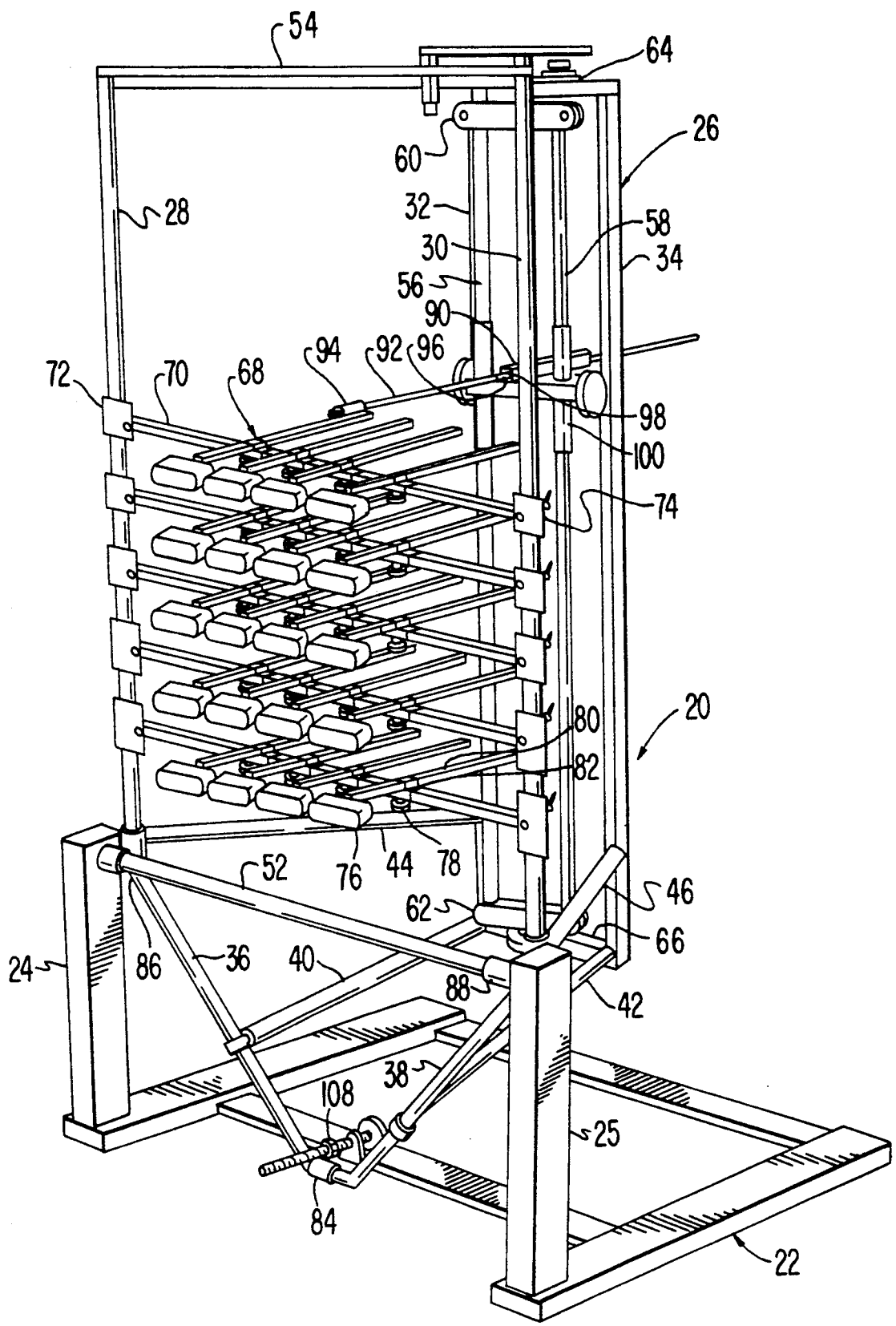
FIG. 1 is a perspective view of the back and trunk positioning and shape sensing apparatus of the invention.

With reference to FIG. 1, there is shown the back and trunk positioning and shape sensing apparatus 20 of the present invention. The apparatus is supported by a support base 22 having support uprights 24 and 25. To these uprights, there is pivoted a tiltable frame 26 which includes front parallel vertical tubes or rods 28 and 30, and rear parallel vertical tubes or rods 32 and 34.

Converging adjustment tubes 36 and 38 extend from their top which is connected to the lower end of the front parallel vertical tubes or rods, and converge downward to their bottom end where they meet with an adjusting mechanism to be later described.

The front vertical tubes 28 and 30 are spaced apart from the rear vertical tubes 32 and 34 in a fore-and-aft position by lower inclined connecting tubes 40 and 42 which are connected at their fore, or front, position to the converging adjustment tubes and at their rear position at the bottom of the rear vertical tubes; by intermediate horizontal connecting tubes 44 and 46 and by upper horizontal connecting tubes 48 and 50. The front vertical tubes are connected transversely by a lower transverse front tube or rod 52 and an upper transverse tube or rod 54. The rear vertical tubes are connected transversely by an upper transverse rear short tube 64 and a lower transverse short tube 66.

The shape sensing mechanism or assembly 90 is carried by two vertical parallel rotating tubes 56 and 58 which are spaced apart by an upper rotating cross member 60 and lower rotating cross member 62.

There are 20 adjustable pad assemblies 68 for positioning the back and trunk of the person being measured. The number of pad assemblies can of course be varied as desired. The adjustable pad assemblies are carried by five horizontal transverse adjustment bars or horizontal bars 70 which are attached at each end by an adjustment bar slider 72 and 74 which respectively are adapted to slide in a vertical direction on front vertical tube 28 and 30. Each adjustable pad assembly 68 includes a pad 76 and a pad pivot 78, both carried at the front end of a pad support rod 80, which slides in a support rod transverse and extension slide-and-lock 82.

Figure 2:
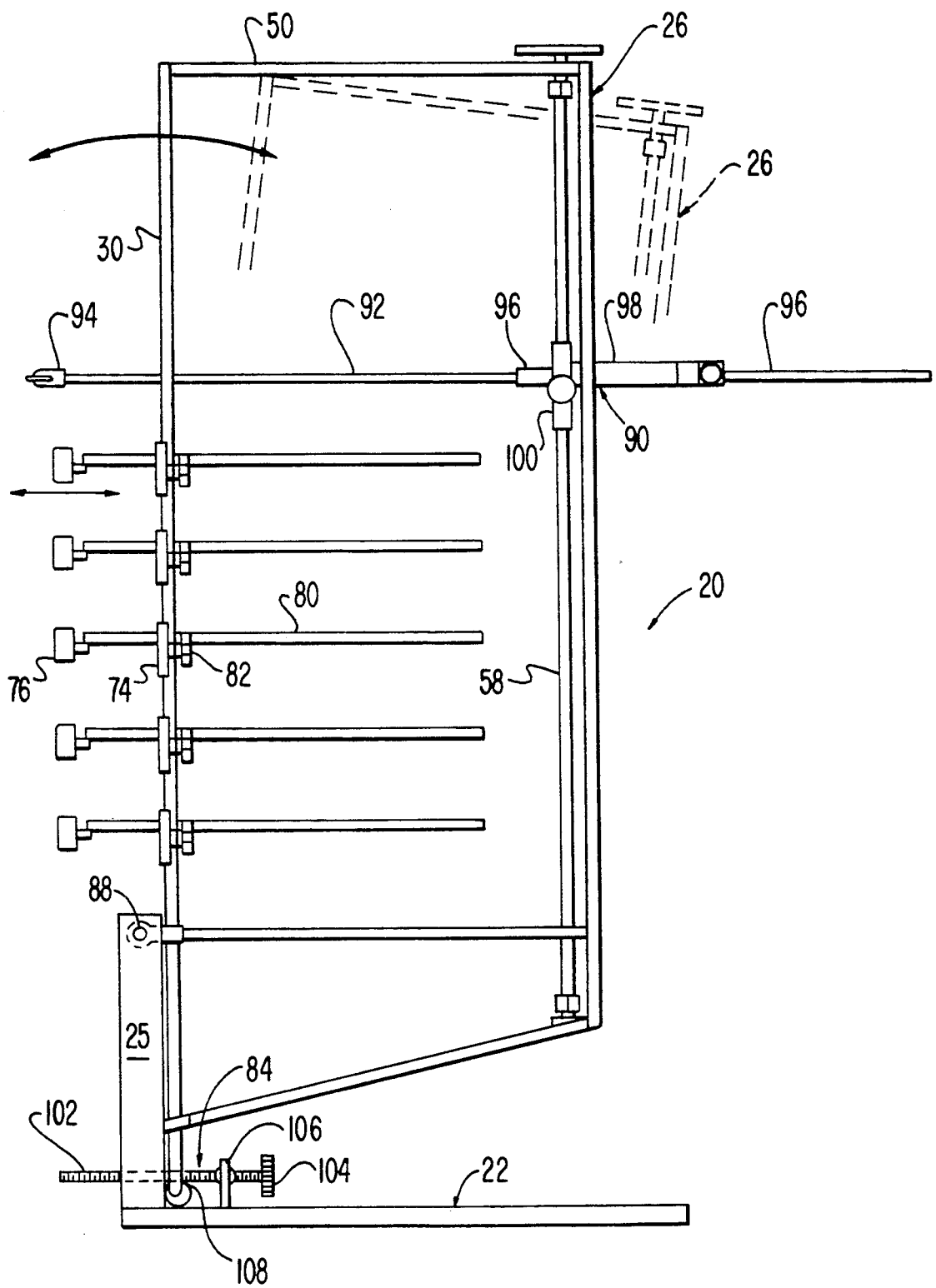
FIG. 2 is a schematic side view of the apparatus of FIG. 1, showing the tilting of the apparatus in dotted lines.

The entire frame 26 may be tilted over a range of preferably approximately 12°, as best seen by the dotted lines of FIG. 2 representing a tilted position. The tilting occurs when frame 26 pivots about lower transverse front connecting tube 52, which acts as an axle, with its left end rotating in tilt pivot 86 mounted on support upright 24, and its right end rotating in tilt pivot 88 mounted on support upright 25. The pivoting is carried out by the tilt adjust assembly 84.

The shape sensing assembly 90 includes a contact arm 92 which also may also be referred to as a measurement rod, extension rod, or probe rod. The contact arm carries at its foremost end a contact sensor 94. The contact arm is attached to contactor arm support 96, which slides in a contact arm support slider 98 for horizontal extension adjustment. The contact arm and contactor arm support may be referred to as the elongated sensor support. The slider 98 is carried by H-shaped cross-bar 130 and contact ar support sliders 100 for vertical adjustment.

The preferred overall dimensions of the invention for positioning and shape sensing of a majority of patients is as follows: the tilt points 86 are approximately 17 inches off the ground; the transverse dimensions as measured by the length of the upper front tube 54 and lower front tube 52 are approximately 31 inches; the height as measured by the length of the rear vertical tubes 32 and 34 is approximately 51½ inches; and the rear vertical tubes 32 and 34 are separated from each other by transverse rear tubes 64 and 66 which are approximately 10½ inches in length.

While the various tubes and rods may be made up of any suitable material, they are preferably made of round 13/16ths inch and square 1 inch steel tubing, with the horizontal transverse adjustment bars being made from ¾ inch square stainless steel tubing. The tube and rods are connected together preferably by welding, or when disassembly is desired, by mechanical joints.

The overall apparatus as shown in FIGS. 1 and 2 has been generally described with reference to the main components. Now a more detailed explanation of these components will be pointed out with reference to the most illustrative figures.

The tilting arrangement of the invention is best seen with reference to FIG. 1, 2 and 5. The entire frame 26 moves as a unit about the tilt pivots 86 and 88, as dictated by the tilt adjustment assembly 84. The tilt adjustment assembly includes an elongated threaded screw 102 having at one end a knob 104 so that the screw can be rotated by hand. The screw is maintained in a stationary position by means of a support 106. The support 106 permits the screw to rotate but not move in a longitudinal direction, although a slight amount of pivoting is permitted. The screw is threadingly engaged with a threaded nut 108 carried by the lower converged ends of converging adjustment tubes 36 and 38.

The first step in making a back and trunk contour for a person would be to have them sit in front of the apparatus shown in FIG. 1 (seat not shown) with their back and trunk engaged by the apparatus. Then the frame of the apparatus may be tilted independently from the seat plane upon which the person is seated. The adjustment may be made over a range of approximately 12°, but it can be greater than that if desired. Initially a vertical position is assumed, and in some cases no tilting of the frame would be utilized. The frame is tilted by manually turning the knob, which through the threaded nut causes the entire frame to tilt, as shown by the dotted lines of FIG. 2. It is to be noted that the entire frame is tilted so that the later measurements using vertical, extended and angular positions of the sensor when it touches the back and trunk will stay the same with respect to one another.

Figure 3:
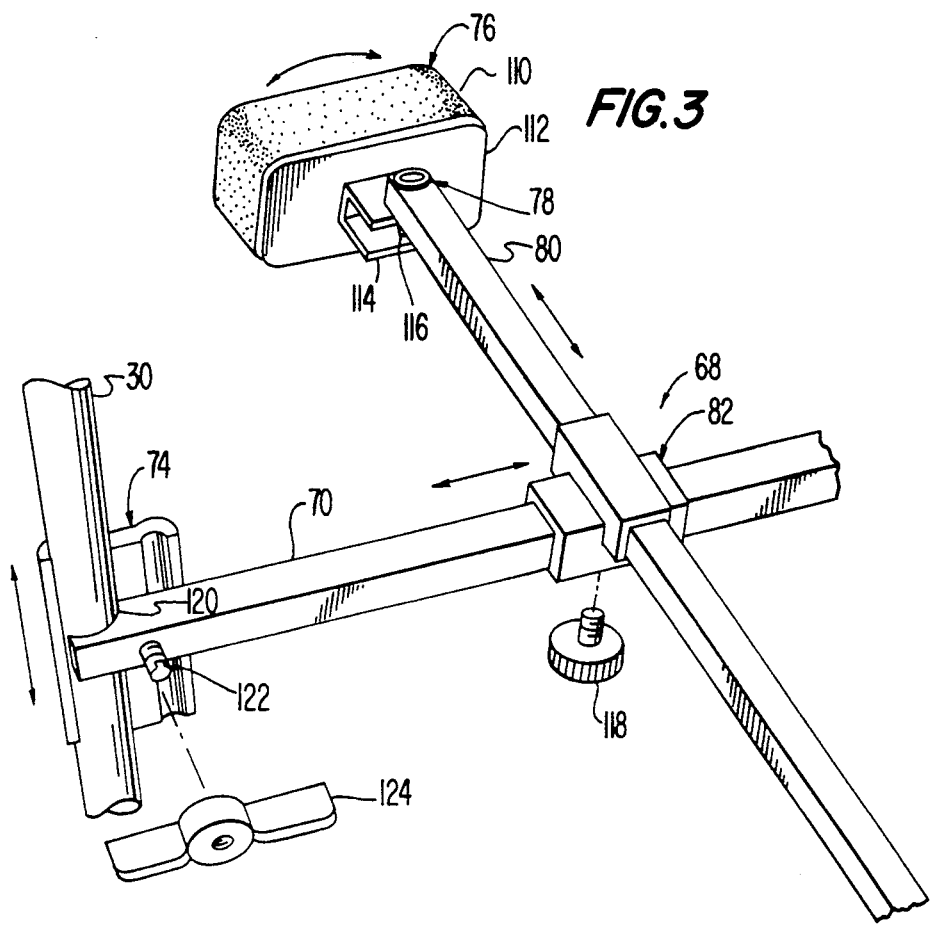
FIG. 3 is a partial perspective view showing the adjustability of the pads and their supporting mechanism for back and trunk positioning.

The pads used for back and trunk positioning are best seen in FIGS. 1, 2 and 3. The adjustable pad assemblies 68 are each identical, and include a soft foam pad 76 having a piece of foam 110 adhered to an aluminum backing plate 112. Mounted to the rear of the backing plate is a pad pivot arrangement 78 consisting of a pivot bracket 114 mounted to the plate pivoted about a pivot pin 116 carried by pad support rod 80 at its outermost front end. The pad support rod is a rectangular stainless steel tubing which slides in a connector or support rod transverse and extension slide-and-lock 82. It extends backward and forward or fore and aft in a linear direction through a fore and aft rectangular opening in the slide. Thus, it is free to extend but not to rotate.

The slide 82 slides in a transverse direction along horizontal bar 70 which is also rectangular, so the slide is free to move in a transverse direction but is not free to rotate. Screwed into the bottom of the slide is a locking screw and knob 118. It is threadingly received in the bottom wall of the slider 82, and when screwed inward, contacts the bottom wall of horizontal bar 70 to lock the slider from further movement. When unscrewed, the slider is unlocked and is free to be adjusted in a transverse direction. Also, the slider has an opening between the transverse rectangular opening that slides along the horizontal bar 70 and the extension or fore and aft opening through which the pad support rod 80 extends. This opening is dimensioned in such a manner that the bottom of pad support rod 80 rests on the top of horizontal bar 70 so that when the locking screw and knob are tightened, the support rod 80 and the horizontal bar 70 are pulled and clamped together and rod 80 is locked from any further adjustment.

The ends of the horizontal bar 70 have a shape 120 to partially encircle vertical tube 30. Also partially encircling vertical tube 30 is adjustment bar slider 74 which is contoured to fit the shape of tube 30, and also carry locking screw 122. The screw extends through an aperture in horizontal bar 70. A locking wing nut 124 is manually screwed onto locking screw 122, and when tightened, pulls slider 74 and horizontal bar 70 towards one another to clamp around vertical tube 30 to lock the horizontal bar 70 from any further vertical adjustment. When vertical adjustment is desired, the locking wing nuts at each end of the vertical bar 70 are loosened, the adjustment made, and then the wing nuts retightened.

There are a series of parallel horizontal bars spaced from another. They are adjusted in a manner to properly position the person whose shape is to be measured. The space between the bars is an elongated horizontal opening that provides access to a contact sensor for measuring the shape of the positioned trunk and back. The shape or person being measured spans the elongated horizontal openings so that the surface of the shape or person is sensed to measure the contour. This positioning and holding in place of the trunk and back for measurement is especially important in providing the proper posture for some handicapped people.

Thus, the positioning pads have three degrees of freedom. They can be extended inwardly and outwardly, can move in a vertical direction, can be moved in a transverse direction. They may be considered as having a fourth degree of freedom in as much as the pads can be tilted about a horizontal plane to accommodate the localized shape of the trunk and back at a support point.

Once the person has been suitably positioned, a series of measurements are made of the back and trunk to determine the three-dimensional contours thereof. These are point measurements which when connected together form the contours. The shape sensing assembly 90 is utilized for making these point determinations for creating the contours.

The shape sensing assembly is best seen in FIGS. 1, 2, 6, 7, 8 and 11, and consists of a contact arm 92 which is supported by and an extension of contactor arm support 96. The contactor arm support 96 carries inserted on its top surface a rack 126 which mates with a pinion 128. The rack and contactor arm support are rectangular in cross section, and slide in a rectangular opening or tunnel in slider 98. This permits a non-rotating horizontal extension for adjustment.

The slider 98 is supported by cross bar 130 which has a slider 100 at each end for sliding vertically on parallel rotating tubes 56 and 58 for vertical adjustment. The cross-bar 130 and two sliders 100 form a letter H shape.

At the outermost end of the contactor arm 92 is a contact sensor 94 which may be a simple rounded pointer, but preferably is a wheel or roller 132 carried by pin 134 extending across slot 136 and wheel support 138. The wheel is adapted to rotate about the vertical axis around vertically extending pin 134.

The diameter of the sensing wheel 132 is chosen of a size that can be used to sense the shape of both a back and trunk or a cast of a back and trunk, which means it needs to be capable of sensing either a convex or a concave surface. When sensing a person, it is a function of the width of the person. As a larger person requires the contact arm to be fully extended, it is necessary that the diameter of the wheel permits it to go around the extreme sides of the person without the contact arm hitting the person's side. In this case a larger wheel would be used, such as a two-inch wheel. Normally the wheel is one-inch in diameter. The may be in the form of a rounded end without a wheel when measuring the concave surface of the inside of a cast of a torso.

The contact arm support 96, because of being square in cross-section, is not free to rotate in the rectangular aperture or tunnel in slider 98, but it is free to extend in a horizontal direction. The inside of the tunnel in slider 98 is lined with a suitable plastic material so as to minimize friction while permitting ease of the horizontal extension of the contact arm support 96. The rack 126 is inserted below the top surface of support 96 so that it will not interfere with the extension of the support.

The contact sensor support arm is 15 inches long and the slider 24 inches long. The rack portion of the slider is 17 inches long.

The shape sensing assembly is moved in a vertical direction by vertically moving the cross bar 130 and slider 100 up and down on parallel rotating tubes 56 and 58. The tubes 56 and 58 are connected at their top by upper rotating cross member 60, and at their bottom by lower rotating cross member 62. At the center of upper rotating cross member 60, there is provided an upper pivot pin 140, and at the center of lower rotating cross member 62 there is provided a lower pivot pin 142. Both pivot pins have a vertical axis, and the upper pin 140 is supported by upper pivot 144 and lower pivot pin 142 is supported by lower pivot 146. Thus, the contactor arm is free to rotate about a vertical axis, as shown by the dotted lines of FIG. 7.

A shape is sensed by adjusting the extension of the contact sensor along a horizontal plane; by the vertical adjustment of the location of that horizontal plane by vertically adjusting the slider 100 along the vertical parallel rotating tubes 56 and 58, and by rotating the contactor arm support to the proper direction or angle. The preferred method for recording the position of the contact sensor 94 is by means of precision rotary potentiometers which transduce the physical position of the three degrees of freedom of the adjustment of the contact sensor 94 to an electrical analog signal. These three degrees of freedom are the sensor's vertical position, the extended length of the sensor, and the angular position (transverse position) of the sensor. The use of precision potentiometers is a well-known electromechanical position measuring technique, and it needs no detailed description here. Other equivalents such as optical shaft encoders may also be used. This electrical analog signal can be digitized and used in a computer, or used merely to indicate the actual measurements of the vertical position, extended position, and angular position. Preferably the electrical potentiometer is of the rotary type that has ten turns of its shaft to cover the full range of measurements. These are available from a number of different sources, and it is merely a matter of choice of a person skilled in the art as to selecting and ordering an appropriate potentiometer.

Figure 4:
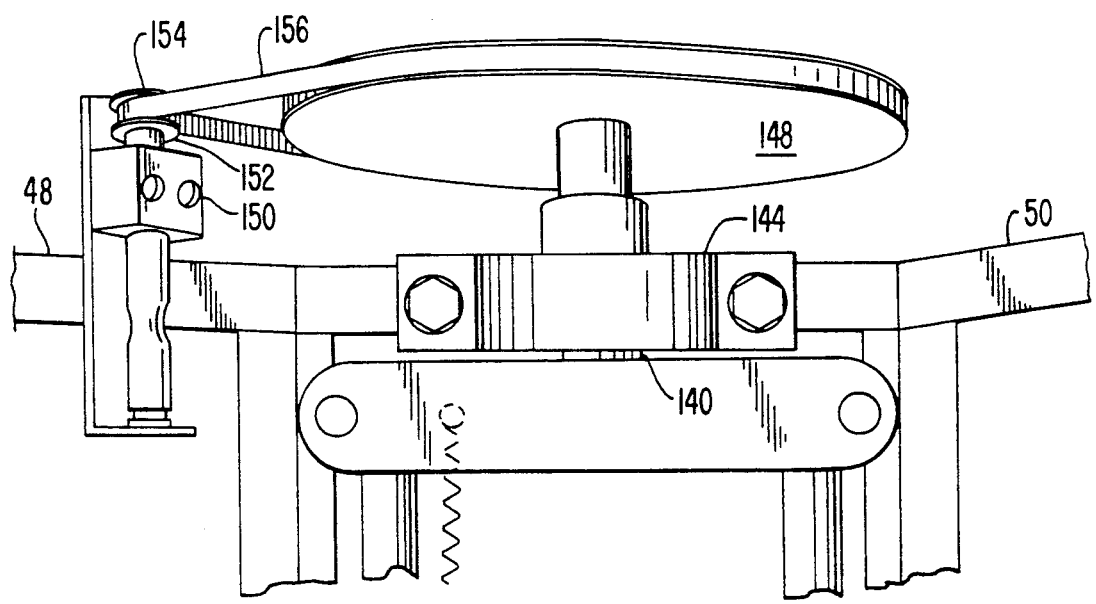
FIG. 4 is a perspective view of part of the top of the apparatus of FIG. 1 showing the manner by which the angle of the shape sensor is determined by a potentiometer.
Figure 9:
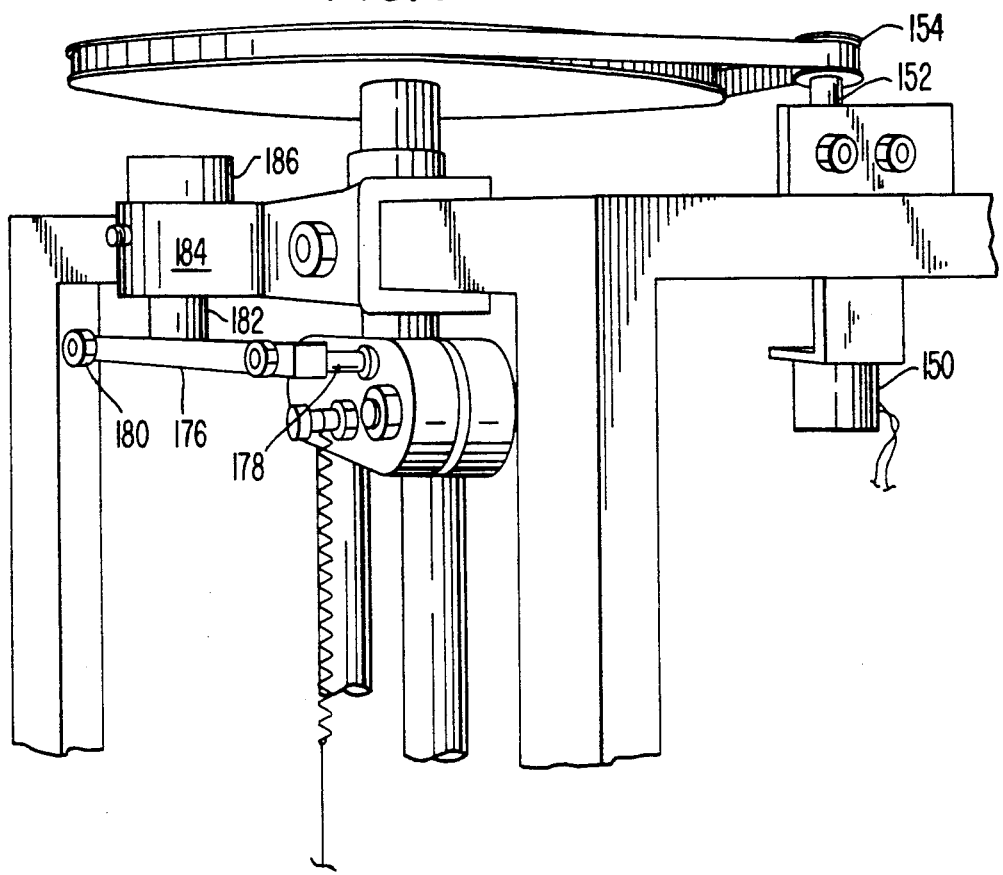
FIG. 9 is another perspective view, somewhat similar to FIG. 4, showing the angle measurement of the shape sensor and the stops and calibration arrangement.
Figure 10:
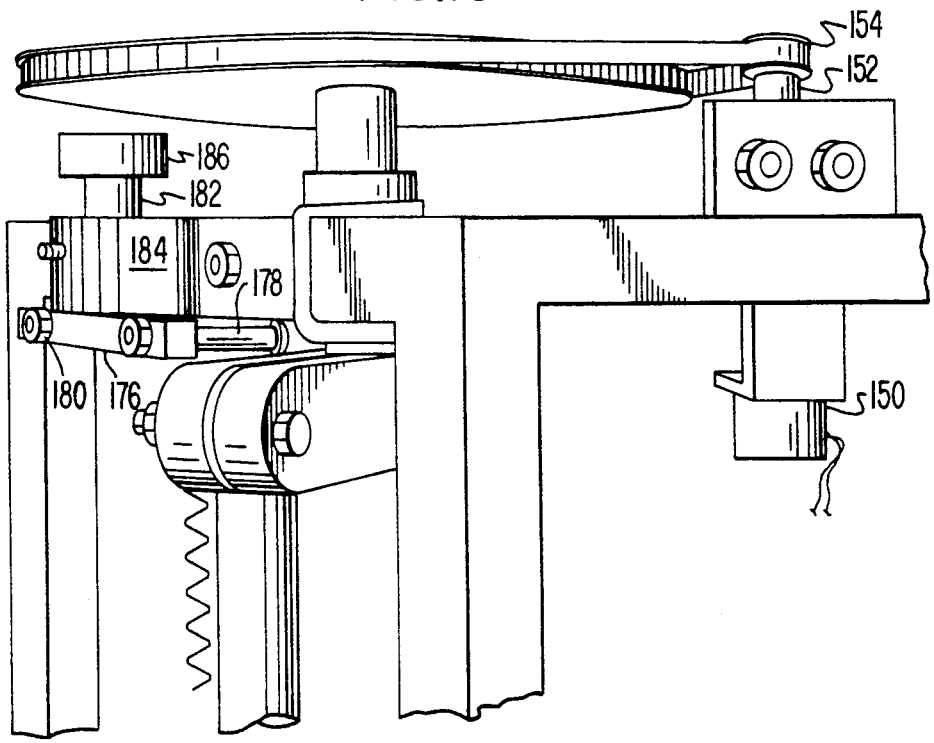
FIG. 10 is a view similar to FIG. 9, but showing the stops for the calibration arrangement in a disengaged position.

The way the three measurements are made is best shown in FIGS. 4, 6, 7, 9, 10 and 11. The angular measurement is best shown in FIGS. 4, 9 and 10, where the upper pivot pin 140 extends through upper pivot 144 and has mounted on its upper end a timing belt pulley 148. Mounted on the upper horizontal connecting tube 48 is the angle position measuring potentiometer 150 having a vertically extending shaft 152 surmounted by a small timing belt pulley 154. The timing belt 156 extends around the small timing belt pulley 154, and the large diameter timing belt pulley 148 so that the pivoting of contact sensor 94 translates into an angular movement about a vertical axis of upper pivot pin 140 which causes the large diameter timing belt pulley 148 to rotate, which in turn causes the timing belt 156 to move and rotate the small timing belt 154 which rotates the shaft 152 and the potentiometer 150 so as to have an electrical measurement of the angular position of the contact sensor 94.

Figure 11:
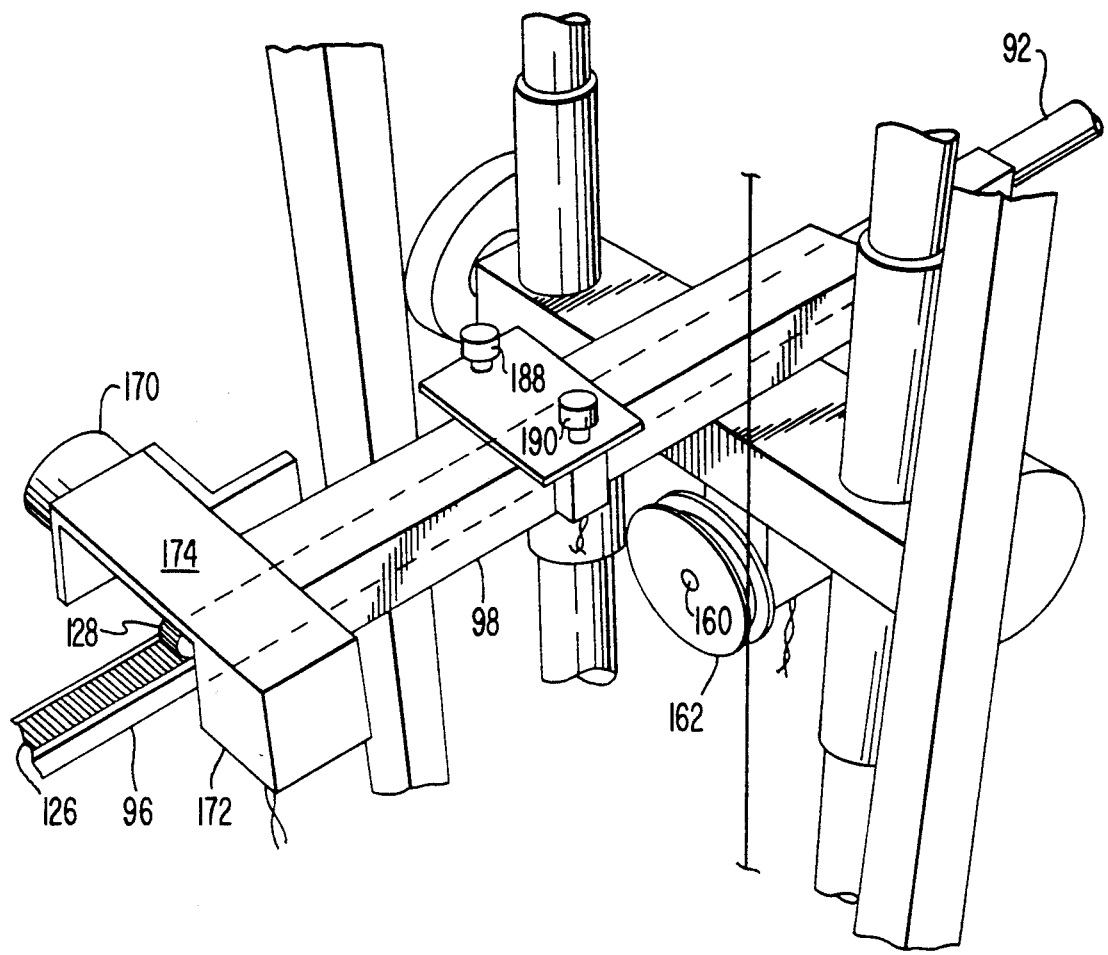
FIG. 11 is perspective partial view showing the linear adjustment arrangement of the shape sensor, as well as the potentiometer arrangement for the vertical measurement.

The vertical measurement of the location of the contact sensor 94 is best illustrated in FIGS. 6 and 11. A vertical height position measuring potentiometer 158 has a horizontal shaft 160 on which is mounted a pulley 162. The potentiometer 158 is attached to the cross bar 130. A vertical wire 164 is wrapped around pulley 162 and has one end attached to the lower rotating cross member 62 and the other end attached to a coil tension spring 166, which in turn is attached to upper rotating cross member 60. As the H-shaped slider 100 and cross bar 130 are adjusted in a vertical direction, the vertical wire 164 remains relatively stationary, and causes the pulley 162 to rotate with the vertical movement. The vertical wire 164 is held in frictional engagement with the pulley 162 by the tension applied through coil spring 166 so that the movement of the pulley 162 is directly related to the vertical movement since the wire is not free to slip on the pulley. As the pulley rotates, it also rotates the horizontal shaft 160 and the resistance element (not shown) in the vertical height measuring potentiometer 158 so that the vertical position is translated to an electrical value by the potentiometer in the well-known manner.

The measurement of the extension of the contact sensor 94 is best shown in FIGS. 2, 7 and 11. An extension length measuring potentiometer 170, which may also be referred to as an electromechanical fore and aft position transducer, is carried by a support 174, which is a part of the contact arm support slider for horizontal extension adjustment 98. The potentiometer 170 has a horizontal extending shaft (not shown) which has attached thereto pinion 128. The shaft is also supported by bearing 172. The pinion is caused to rotate by rack 126 a the contactor arm support 96 moves with the contactor arm 92 as the contact sensor 94 is extended outwardly and inwardly. With the rotation of the pinion, the resistance element (not shown) in the potentiometer 170 is caused to move so that, in the well-known manner, an electrical value is created that is analogous to the amount the contact sensor 94 has been extended.

A calibration feature is provided as shown in FIGS. 9 and 10. A calibration arm 176 is carried at the lower end of a calibration shaft 182, which is adapted to slide in a vertical direction within calibration shaft support 184, but is not free to rotate with respect thereto. At the top of calibration shaft support 184 is a calibration shaft head 186 which prevents the shaft 182 from moving downward beyond a fixed point downward. The head also serves as a means for which the shaft can be moved upward and downward. At both the left and right end of the calibration arm 176 are calibration stops 178 and 180, respectively. Each stop consists of a threaded member extending in a horizontal direction, and held in a threaded hole in the calibration arm. The contact end of the calibration stop is rounded and the other end has a threaded nut which serves to lock the calibration stop in position once it has been extended the amount desired. When the calibration arm is in the downward calibration position such as shown in FIG. 9, the rotation of upper rotating cross member is stopped when it comes into contact with the rounded end of either of the calibration stops through metal-to-metal contact. Thus, the exact position that had been calibrated for the amount of angular movement to that location is known, both on a rotation to the right or a rotation to the left. That value can be used to calibrate the electrical values for that exact and known position. When the calibration device is in the raised position such as shown in FIG. 10, the calibration stops are raised above the upper rotating cross member 60, and therefore permit it to freely rotate to its maximum extent.

With reference to FIG. 11, there are shown two electrical momentary switches, 188 for calibration and 190 for taking measurement points.

When the calibration arm is lowered, and the contact sensor 94 is at the preselected calibration height and extension position, the sensor is rotated until it is stopped by calibration stop 178 or calibration stop 180. Then switch 188 is depressed to close an electrical circuit that measures the analogous electrical values of the three potentiometers which indicate the angular position, extended position, and vertical position of the contact sensor at that calibration point.

When the calibration arm 176 is in the raised position so that the angular movement of the contact sensor is not stopped by the calibration device, then when a measurement is desired the measurement switch or button 190 is depressed, and that is connected to an electrical circuit in a manner that the electrical analog values for the angular position, the extended position and the vertical position of the contact sensor 94 are taken. While a manual method of taking the values is illustrated, as stated earlier these values can be automatically digitized and put into a digital computer for further processing. After a person has been suitably positioned in the apparatus of this invention, a series of point measures are made to ascertain the contour shape of the back and trunk. The shape sensing assembly 90 is moved in a vertical direction to the level that the measurements will first start to be taken. While in that position, the contactor arm 92 is moved and extended to the first point on the trunk or back at which measurements are to be taken. In one position, the angle, amount of extension and vertical position at that point ar taken either manually or the information fed into a computer. The contact sensor 94 is moved in a horizontal plane to take a series of additional points in that plane to trace the contour of a back or trunk. Once all the points are taken in that plane, the shape sensing assembly 90 is moved to the next plane and a series of points are measured in that plane.

The plane through the contactor arm 92 is rotated will either be above, below or in between the transverse adjustment bars 70.

Figure 12:
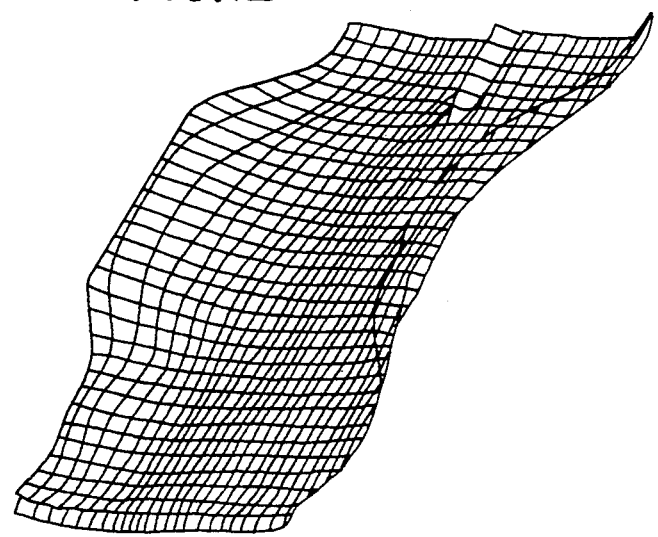
FIG. 12 is a perspective view of a typical back and trunk shape sensed by the apparatus of the invention.

After measuring the necessary number points, a contour is established such as in FIG. 12, where the points are connected together by various lines to show the contour of a back and trunk. The discreet points that are measured are not necessarily measured at regular intervals, but vary as to the intervals based on the general shape of the contour. Generally the horizontal or transverse points are no closer than ¼ inch apart, and they may be as far apart as 1 to 1½ inches. For example, a relatively flat surface would have the measurements taken at less frequent intervals.

It is more important that the intervals at which points are measured be taken more frequently on a horizontal plane than on the vertical plane, since most of the curvature is usually around the rib cage, where the contours are more steep, whereas in a vertical direction from top to bottom the contours are usually less deep and a fewer number of points are satisfactory. Therefore, the horizontal planes across which measurements are taken may be approximately 2½ inches apart.

While the invention is primarily concerned with the measurement of back and trunk contours, as said earlier it can be used to measure a molding of that contour, and can be used to measure other shapes such as a limb segment. Once the contour has been measured, this can be converted into a custom-fitted back support or other applications using well-known techniques such as that set forth in the Brubaker et al. co-pending patent application supra. Generally, when a resilient foam is used for supporting the back, it is more stiff than that used for supporting a seat.

Thus, there is described above an apparatus and system for positioning and sensing the shape of a person's back and trunk. It will be appreciated that other uses can be made of the system such as measuring casts of a back and trunk, or limbs.

Various modifications of the apparatus and system described will be evident to those skilled in the art. The figures and description herein are therefore not to be construed as limitations, but merely constitute a preferred embodiment of the invention, and various changes and modifications may be made without departing from the spirit and scope of the present invention as set forth in the claims herein below.

What is claimed is:

1. A shape sensing apparatus comprising:
   a frame having at least two horizontal openings through which the contours of a shape may be sensed;
   an elongated sensor support capable of an approximately horizontal transverse movement and fore and aft movement;
   a sensor mounted at a fore end of said elongated sensor support adapted to extend into said horizontal openings and sense a surface of the shape when the shape is spanning said openings and move transversely in approximately a horizontal plane to measure a contour of said surface; and
   a vertically adjustable support carried by said frame and carrying said elongated sensor support for adjusting the height of said elongated sensor support.

2. The apparatus of claim 1 wherein said elongated sensor support pivots about an approximately vertical axis when making said horizontal transverse movement.

3. The apparatus of claim 2 wherein there is further included:
   an electromechanical angular position transducer mounted on said frame and adapted to produce an electrical value analogous to the angular position of said sensor.

4. The apparatus of claim 3 wherein:
   said electromechanical angular position transducer is of a rotary type having a small pulley driving a shaft;
   a vertically extending shaft coaxial with the sensor's vertical pivot axis and rotatable with said sensor when it pivots;
   a large pulley mounted on said vertically extending shaft; and
   a belt coupling said large and small pulley to rotate said shaft to said electromechanical angular position transducer as said elongated sensor support and sensor are pivoted in a transverse direction.

5. The apparatus of claim 1 wherein there is further included:
   a positioning system for a shape sensing assembly comprising:
   at least two transverse parallel bars mounted on said frame and vertically spaced from one another;
   at least two position members connected to each of said transverse bars and adapted to be adjusted in a fore and aft direction to position each member into contact with the shape; and
   connectors connecting said members to said transverse bars.

6. The apparatus of claim 5 wherein:
   said connectors include:
   a transverse opening through which said connectors may slide transversely along said transverse bars to adjust the transverse positions of said position members;
   a fore and aft opening through which said position members may slide to adjust their fore and aft position; and
   a locking mechanism for clamping so that said position members may be clamped to said transverse bars to lock said position members in a fixed position.

7. The apparatus of claim 6 where in there is included:
   two approximately vertical front bars forming a side of said frame; and
   a vertical slider at each end of said transverse bars for sliding along said vertical front bars for the vertical adjustment of the height of said transverse bars.

8. The apparatus of claim 9 wherein:
   a soft pad is pivotally mounted to a fore end of each of said position members.

9. The apparatus of claim 7 wherein there is further included:
   a base for supporting said frame having two opposed upright members;
   a pivot point near an upper end of each of said upright members;
   two pivots on said frame for pivotally connecting said frame to said pivot pints; and
   an adjusting mechanism for pivoting said frame about said pivot points until a desired tilt angle is obtained.

10. The apparatus of claim 9 wherein there is further included:
    an electromechanical vertical position transducer mounted on said vertically adjustable support and adapted to move therewith and produce an electrical value analogous to the vertical position of said sensor;
    an electromechanical fore and aft position transducer carried by said vertically adjustable support and adapted to produce an electrical value analogous to the fore and aft extended position of said sensor; and
    an electromechanical angular position transducer mounted on said frame and adapted to produce an electrical value analogous to the angular position of said sensor.

11. The apparatus of claim 10 wherein:

said electromechanical vertical position transducer is of a rotary type having a wheel driving a shaft;

a vertically extending stationary taut wire adapted to be in frictional engagement with said wheel and causing said wheel to rotate as said vertical position transducer is moved up and down with said vertically adjustable support;

said electromechanical fore and aft position transducer is of a rotary type having a pinion driving a shaft;

a rack in engagement with said pinion carried by said elongated sensor support and causing said pinion and shaft to rotate as said elongated sensor support and sensor are moved in a fore and aft direction;

said electromechanical angular position transducer is of a rotary type having a small pulley driving a shaft;

a vertically extending shaft coaxial with said sensor vertical pivot axis and rotatable with said sensor when it pivots;

a large pulley mounted on said vertically extending shaft; and a belt coupling said large and small pulley to rotate said shaft to said electromechanical angular position transducer as said elongated sensor support and sensor are pivoted in a transverse direction.

12. The apparatus of claim 5 wherein said sensor is a wheel rotatably mounted at the fore end of said elongated sensor support.

13. The apparatus of claim 5 wherein there is further included:
an electromechanical vertical position transducer mounted on said vertically adjustable support and adapted to move therewith and produce an electrical value analogous to the vertical position of said sensor.

14. The apparatus of claim 13 wherein:
said electromechanical vertical position transducer is of a rotary type having a wheel driving a shaft; and
a vertically extending stationary taut wire adapted to be in frictional engagement with said wheel and causing said wheel to rotate as said vertical position transducer is moved up and down with said vertically adjustable support.

15. The apparatus of claim 5 wherein there is further included:
an electromechanical fore and aft position transducer carried by said vertically adjustable support and adapted to produce an electrical value analogous to the fore and aft extended position of said sensor.

16. The apparatus of claim 15 wherein:
said electromechanical fore and aft position transducer is of a rotary type having a pinion driving a shaft; and
a rack in engagement with said pinion carried by said elongated sensor support and causing said pinion and shaft to rotate as said elongated sensor support and sensor are moved in a fore and aft direction.

17. A positioning system for a shape sensing apparatus comprising:
a frame;
at least two transverse parallel bars mounted on said frame and vertically spaced from one another;
two approximately vertical front bars forming a side of said frame;
a vertical slider at each end of said transverse bars for sliding along said vertical front bars for the vertical adjustment of the height of said transverse bars;
at least two position members connected to each of said transverse bars and adapted to be adjusted in a fore and aft direction to position each member into contact with a shape;
connectors connecting said members to said transverse bars;
said connectors include:
a transverse opening through which said connectors may slide transversely along said transverse bars to adjust the transverse position of said position members;
a fore and aft opening through which said position members may slide to adjust their fore and aft positions; and p2 a locking mechanism for clamping so that said position members may be clamped to said transverse bars to lock said position members in a fixed position.

18. The apparatus of claim 17 wherein there is further included:
a base for supporting said frame having two opposed upright members;
a pivot point near an upper end of each of said upright members;
two pivots on said frame for pivotally connecting said frame to said pivot pints; and
an adjusting mechanism for pivoting said frame about said pivot points until a desired tilt angle is obtained.

* * * * *